United States Patent
Lazcano-Seres et al.

(10) Patent No.: US 9,120,803 B2
(45) Date of Patent: Sep. 1, 2015

(54) PROCESSES FOR THE PREPARATION OF SODIUM 5,14-DIHYDROTETRAAZAPENTACENE POLYSULFONATE, AND INTERMEDIATES THEREOF

(71) Applicant: Signa S.A. de C.V., Toluca (MX)

(72) Inventors: José Miguel Lazcano-Seres, Calimaya (MX); Cuauhtémoc Carrasco-Pacheco, Toluca (MX); Evin Hazael Granados-Covarrubias, Toluca (MX); Maria De la Luz Reyes-Reyes, Ocoyoacac (MX); Alberto Martinez-Díaz, Ocoyoacac (MX); Roberto Carlos Melgar-Fernández, Metepec (MX); Armando Zambrano-Huerta, Toluca (MX); Maria Viviana Cordero-Pensado, Lerma De Villada (MX); Edson Olimpo Sanchéz-López, Toluca (MX); Omar Gutiérrez-Cajero, Toluca (MX)

(73) Assignee: Signa S.A. de C.V. (MX)

( * ) Notice: Subject to any disclaimer, the term of this patent is extended or adjusted under 35 U.S.C. 154(b) by 0 days.

(21) Appl. No.: 13/912,475

(22) Filed: Jun. 7, 2013

(65) Prior Publication Data

US 2013/0331572 A1    Dec. 12, 2013

(51) Int. Cl.
*C07D 241/38* (2006.01)
*C07D 487/04* (2006.01)

(52) U.S. Cl.
CPC .................................... *C07D 487/04* (2013.01)

(58) Field of Classification Search
CPC .................................................... C07D 241/38
USPC ........................................................ 544/342
See application file for complete search history.

(56) References Cited

U.S. PATENT DOCUMENTS 3,257,402 A    6/1966    Naito

FOREIGN PATENT DOCUMENTS

| GB | 988331 A | 4/1965 |
| WO | 94/29314 A1 | 12/1994 |
| WO | 2007066098 A1 | 6/2007 |
| WO | 2007085810 A1 | 8/2007 |
| WO | 2009083532 A2 | 7/2009 |

OTHER PUBLICATIONS

Armand et al., "Chemical and electrochemical reduction of pyrazino[2,3-g]quinoxalines and of their benzo and dibenzo derivatives; the structure of fluorindine and the formation of tetraanion", Can. J. Chem. 1987, 65, 1619-1623.
Beijing Yixueyuan Xuebao 1980, 12 (4), 262-3,276 (English Abstract provided).
Jenekhe, Samson A., "Electroactive Ladder Polyquinoxalines. 1. Properties of the Model Compound 5,12-Dihydro-5,712,14-tetraazapentacene and Its Complexes", Macromolecules 1991, 24 (1), 1-10.
Ma et al., "Organic thin film transistors based on stable amorphous ladder tetraazapentacenes semiconductors", J. Mater. Chem. 2005, 15, 4894-4898.
Seillan et al., "Efficient Synthesis of Substituted Dihydrotetraazapentacenes", Organic Letters 2008, 10 (18) 4013-4016.
Tang et al., "Benzenoid and Quinonoid Nitrogen-Containing Heteropentacenes", Chemistry—A European Journal 2009, 15 (16), 3965-3969.
Wanzlick et al., "Syntheses with nascent quinones, IV1)", Chem. Ber, 1968, 101(11), 3744-3752.

*Primary Examiner* — Douglas M Willis
(74) *Attorney, Agent, or Firm* — Lerner, David, Littenberg, Krumholz & Mentlik, LLP

(57) ABSTRACT

This invention relates to processes for the preparation of sodium 5,14-dihydrotetraazapentacene polysulfonate (1), and intermediates thereof.

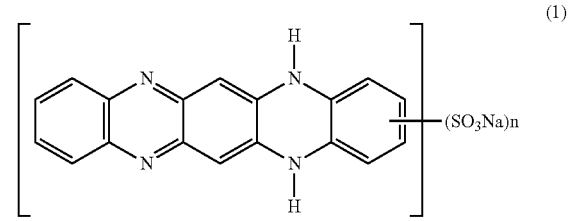

where n = 3 to 5

6 Claims, No Drawings

PROCESSES FOR THE PREPARATION OF SODIUM 5,14-DIHYDROTETRAAZAPENTACENE POLYSULFONATE, AND INTERMEDIATES THEREOF

CROSS-REFERENCE TO RELATED APPLICATIONS

The present application claims the benefit of the filing date of U.S. Provisional Patent Application No. 61/656,615 filed Jun. 7, 2012, the disclosure of which is hereby incorporated herein by reference.

TECHNICAL FIELD

This invention relates to the field of chemical synthesis of organic compounds and in particular to the synthesis of sodium 5,14-dihydrotetraazapentacene polysulfonate, and intermediates thereof.

BACKGROUND

Disodium-5,14-dihydro-5,7,12,14-tetraazapentacene-2,9-disulfonate belongs to a class of azapentacenes known to be useful as an anticataract agent. It has been marketed under the trade names Lutrax™ and Quinax™.

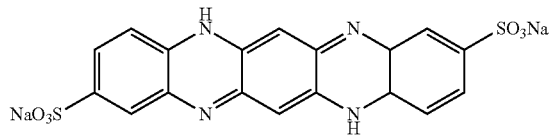

Org. Lett. 2008, 10 (18), 4013-4016 discloses the synthesis of substituted dihydrotetraazapentacenes (DHTAPs) in which the 2,5-dihydroxy-p-benzoquinone is reacted with various substituted o-diaminobenzenes in alcohol (or water) to afford 2,3-dihydroxyphenazines which are reacted with an excess of substituted o-diaminobenzenes in the presence of glacial acetic acid for 24 h, yielding the corresponding substituted DHTAP derivatives. Additionally, a structural study by NMR spectroscopy showed that the conjugated π-system of the pentacyclic skeleton tautomerizes depending on the electronic effect of the substituent(s).

WO2009083532 relates to a method for the preparation of substituted dihydrotetraazapentacenes (DHTAPs), said method comprising the reaction of 2,3-dihydroxyphenazines with o-diaminobenzenes, in the presence of a catalytic amount of an acid.

WO 94/29314 discloses a process for the preparation of materials with the azapentacene core which have electro active properties as well as the use thereof. A phenylenediamine is reacted with a quinone under slightly acidic conditions at reflux.

WO 2007/066098 discloses a process for the preparation of organic acids that are used for the preparation of organic ionic-crystalline photoelectric layer, in which 2,5-dihydroxy-p-benzoquinone is reacted with o-phenylenediamine and 3,4-diaminobenzoic acid in acetic acid.

WO 2007/085810 discloses a conjugated planar heterocyclic system that is a dye with a structure based on quinoxaline or which comprises quinoxaline or a derivative thereof.

J. Mater. Chem. 2005, 15, 4894-4898, describes organic thin film transistors (OTFTs) synthesis based on amorphous films of 5,7,12,14-tetraazapentacene, as well as their improved condensation process, where they were prepared by a one-step condensation reaction between 2,5-dihydro-p-benzoquinone and o-phenylenediamine in absolute ethanol with glacial acetic acid as catalyst.

Can. J. Chem. 1987, 65, 1619-1623, teaches the chemical and electrochemical reduction of the N-heterocyclic compounds, fluorindine derivatives.

Macromolecules 1991, 24 (1), 1-10, reports studies of the structural and physicochemical properties of a model compound of ladder polyquinoxalines, 5,12-dihydro-5,7,12,14-tetraazapentacene (DHTAP), including X-ray diffraction, morphology, spectroscopy, electrochemistry, complex formation, and electrical conductivity.

Chemistry-A European Journal 2009, 15 (16), 3965-3969, describes the debate on the structure of dihydro-5,7,12,14-tetraazapentacene; both the benzenoid and the quinonoid nitrogen-containing heteropentacenes were successfully isolated and investigated on their molecular and electronic structures, molecular packing, and semiconductor properties.

Beijing Yixueyuan Xuebao 1980, 12 (4), 262-3,276 discloses a method for the synthesis of 5,12-dihydro-5,7,12,14-tetraazapentacene-2,9-disulfonate (or Phacolysine), Its active component is the intermediate 5,12-dihydro-5,7,12,14-tetraazapentanece. This intermediate is purified by recrystallization from glacial acetic acid and then sublimed under high vacuum.

Chem. Ber, 1968, 101(11), 3744-3752 discloses preparation of florindin from o-quinones and o-diaminobenzene.

GB 988,331 discloses 5,12-dihydro-5,7,12,14-tetraazapentacene sulfonic acid and its sodium and potassium salts for cataract curatives, and processes for the preparation thereof. 5,12-Dihydro-5,7,12,14-tetraazapentacene and fuming sulfuric acid or chlorosulfonic acid are reacted in the presence of mercuric oxide or mercuric sulfate to provide mono- and di-sulfonic acids of 5,12-dihydro-5,7,12,14-tetraazapentacene.

FR 1,336,438 discloses a process for the preparation of 5,12-dihydro-5,7,12,14-tetraazapentacene sulfonic acid, its alkaline salts and processes for the preparation thereof. 5,12-Dihydro-5,7,12,14-tetraazapentacene and fuming acid, sulfuric acid or chlorosulfonic acid are reacted in the presence of a mercury compound to furnish mono- and di-sulfonic acids of 5,12-dihydro-5,7,12,14-tetraazapentacene.

U.S. Pat. No. 3,257,402 discloses a process for the synthesis of 5,12-dihydro-5,7,12,14-tetraazapentacene sulfonic acids and their alkaline salts, their use as cataract curatives, and processes for the preparation thereof. 5,12-Dihydro-5,7,12,14-tetraazapentacene and fuming sulfuric acid or chlorosulfonic acid are reacted in the presence of mercury oxide or mercury sulfate as catalyst. In this way, mono- and di-sulfonic acids of 5,12-dihydro-5,7,12,14-tetraazapentacene are produced.

JP38001645 discloses preparation of potassium 5,12-dihydro-5,7,12,14-tetraazapentacene-2(or 9)-sulfonate and the potassium and sodium salts of 5,12-dihydro-5,7,12,14-tetraazapentacene-2,9-disulfonic acid.

SUMMARY

The present invention is directed to, but not limited to, methods of preparing an azapentacene compound, sodium 5,14-dihydro-5,7,12,14-tetraazapentacene polysulfonate (1), and intermediates thereof.

In one embodiment, we have unexpectedly discovered that o-phenylenediamine may be coupled with 2,5-dihydroxy-1,4-dibenzoquinone in the presence of a high-boiling alcohol solvent such as benzyl alcohol in a "one-pot" process which does not require isolation and purification of any intermediate, without the need for acid or a catalyst as taught in the prior art (*J. Mater. Chem.*, 2005, 15, see page 4895). Also, we found that there is not a requirement for high volumes of the solvent employed.

Although the present invention is not limited to any particular intermediate, it is postulated that the aforementioned "one-pot" process proceeds via the pathway shown in Scheme 1.

In illustrative embodiments of the present invention, 5,14-dihydrotetraazapentacene and the intermediates thereof may be prepared by an exemplary process as set out in Scheme 1. Exemplary reagents and conditions for these reactions are disclosed herein.

with a compound of Formula 5:

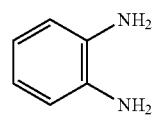

(5)

to provide a compound of Formula 3.

Scheme 1

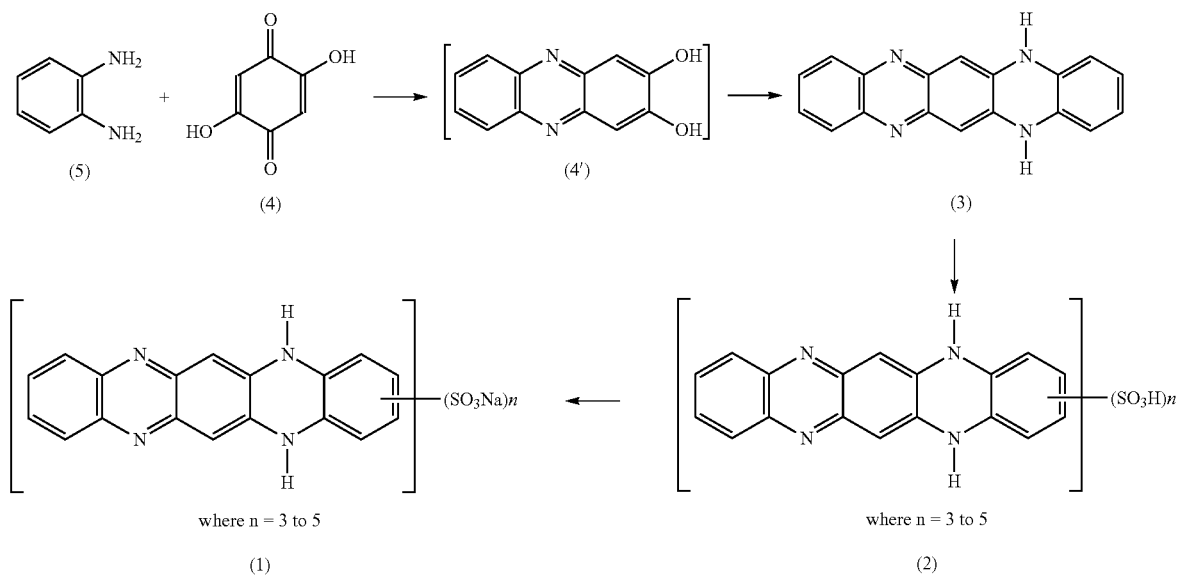

In illustrative embodiments there is provided a one-pot process for the preparation of 5,14-dihydro-5,7,12,14-tetraazapentacene of Formula 3:

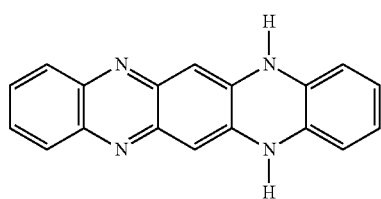

(3)

the process comprising reaction, in a high-boiling alcohol solvent, of a compound of Formula 4:

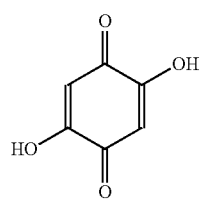

(4)

In illustrative embodiments there is a provided a process described herein wherein the high-boiling alcohol is selected from the group consisting of benzyl alcohol, n-butanol, n-pentanol, cyclohexanol, glycol, diethylene glycol, polyethylene glycol and mixtures thereof.

In illustrative embodiments there is a provided a process described herein wherein the high-boiling alcohol is benzyl alcohol.

In illustrative embodiments there is a provided a process described herein wherein up to 12 volumes of benzyl alcohol is used.

In illustrative embodiments there is a provided a process described herein wherein the compound of Formula 3 is isolated by the addition of a co-solvent selected from the group consisting of aliphatic alcohols and mixtures thereof.

In illustrative embodiments there is a provided a process described herein wherein the co-solvent is ethanol.

In illustrative embodiments there is a provided a process described herein wherein the compound of Formula 3 is further converted to disodium-5,14-dihydro-5,7,12,14-tetraazapentacene-2,9-disulfonate.

In illustrative embodiments there is a provided a process for the preparation of a compound of the Formula 1:

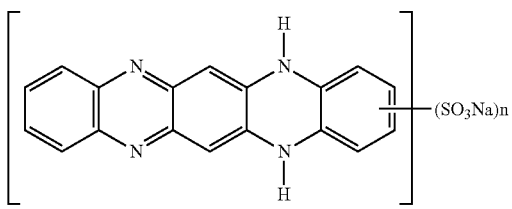

(1)

where n = 3 to 5 the process comprising: a. reaction of a compound of Formula 3:

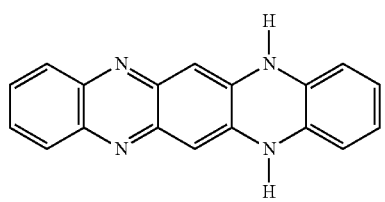

(3)

with a sulfonating agent to provide a compound of Formula 2:

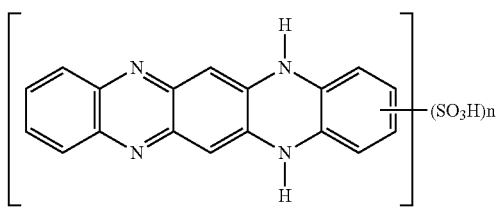

(2)

where n = 3 to 5 b. reaction of a compound of Formula 2 with a base to provide a compound of Formula 1.

In illustrative embodiments there is a provided a process described herein wherein the sulfonating agent is selected from the group consisting of sulfuric acid, chlorosulfonic acid and mixtures thereof.

In illustrative embodiments there is a provided a process described herein wherein the sulfonating agent is chlorosulfonic acid.

In illustrative embodiments there is a provided a process described herein wherein the sulfonating agent is also acting as a solvent.

In illustrative embodiments there is a provided a process described herein wherein the base is selected from the group consisting of sodium hydroxide, sodium methoxide, sodium carbonate and sodium bicarbonate.

In illustrative embodiments there is a provided a process described herein wherein the base is sodium hydroxide.

In illustrative embodiments there is a compound of Formula 2a and salts thereof:

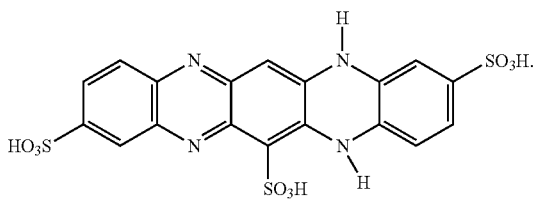

(2a)

In illustrative embodiments there is a compound of Formula 2a' and salts thereof:

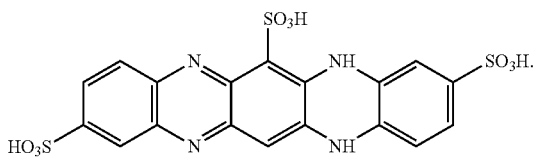

(2a')

In illustrative embodiments there is a compound of Formula 2b and salts thereof:

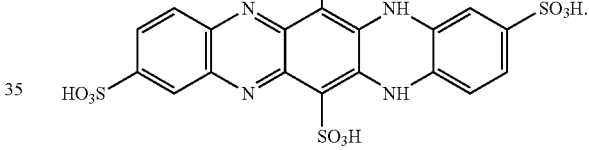

(2b)

In illustrative embodiments there is a compound of Formula 2c and salts thereof:

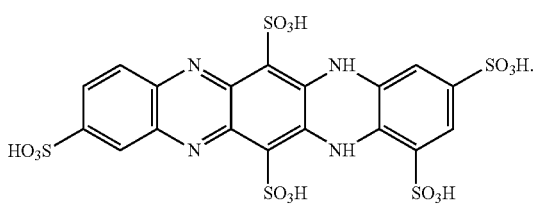

(2c)

In illustrative embodiments there is a compound of Formula 1a:

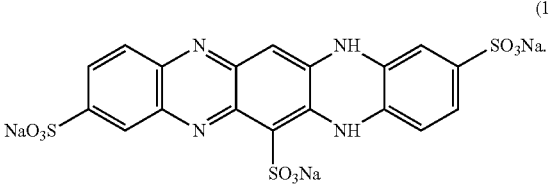

(1a)

In illustrative embodiments there is a compound of Formula 1a':

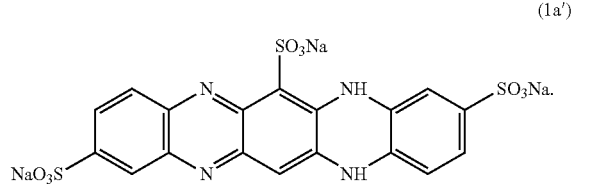
(1a')

In illustrative embodiments there is a compound of Formula 1b:

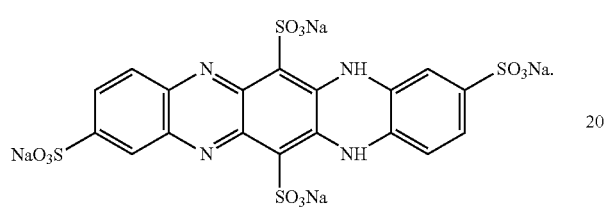
(1b)

In illustrative embodiments there is a compound of Formula 1c:

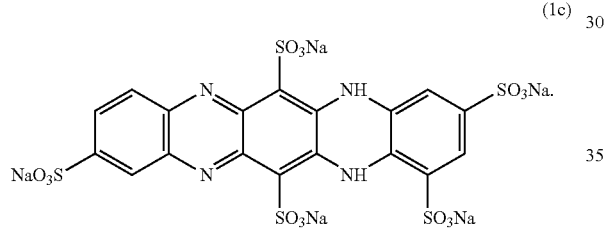
(1c)

Other aspects and features of the present invention will become apparent to those ordinarily skilled in the art upon review of the following description of specific embodiments of the invention.

DETAILED DESCRIPTION

As used herein, the term "aliphatic" by itself or as part of another substituent, means, unless otherwise stated, a saturated straight or branched chain, or cyclic hydrocarbon radical, or combination thereof, having the number of carbon atoms designated (e.g. $C_1$-$C_{10}$ or 1- to 10-membered means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like.

As used herein, the term "salt" may be a suitable base-addition salt of a compound with an alkali metal salt (e.g. lithium, sodium or potassium), an alkaline earth metal salt (e.g. calcium or magnesium), an ammonium salt or a salt with an organic base (e.g. methylamine, dimethylamine, trimethylamine, piperadine or morpholine).

According to illustrative embodiments of the present invention, there is provided a one-pot process for the preparation of 5,14-dihydrotetraazapentacene of Formula 3:

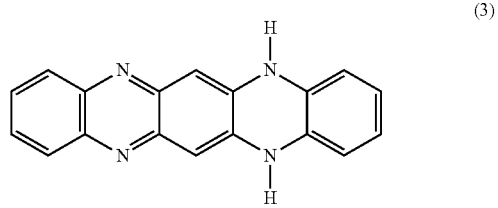 [SMILES: c1ccc2c(c1)Nc1cc3nc4ccccc4nc3cc1N2]
(3)

the process comprising reaction, in a high-boiling alcohol solvent, of a compound of Formula 4:

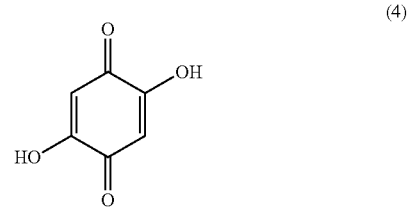
(4)

with a compound of Formula 5: to provide a compound of Formula 3.

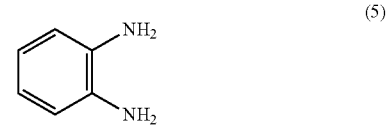
(5)

The high-boiling alcohol solvent may be selected from the group consisting of benzyl alcohol, n-butanol, n-pentanol, cyclohexanol, glycol, diethylene glycol, polyethylene glycol and mixtures thereof.

In the reaction of a compound of Formula 4 with the compound of Formula 5, the amount of the compound of Formula 5 may range from about 2 to about 10 equivalents relative to the compound of Formula 4.

The reaction of the compound of Formula 4 with the compound of Formula 5, may be performed at a temperature ranging from about 80° C. to about 150° C., preferably from about 110° C. to about 135° C.

In an embodiment, in the reaction of the compound of Formula 4 with the compound of Formula 5, the product may be isolated by addition of a suitable co-solvents selected from the group consisting of aliphatic alcohols (e.g. ethanol, methanol, isobutyl alcohol, isopropyl alcohol) and mixtures thereof. The most preferred co-solvent is ethanol.

In illustrative embodiments of the present invention, there is provided a process for the preparation of a compound of the Formula 1:

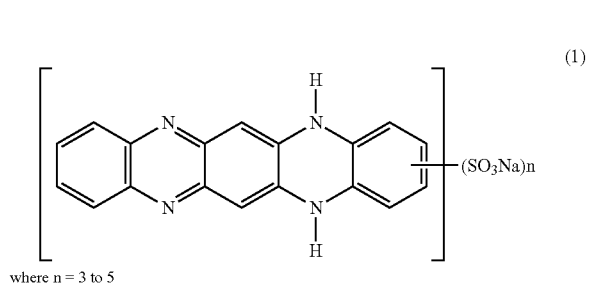
(1)

where n = 3 to 5 the process comprising:

a. reaction of a compound of Formula 3:

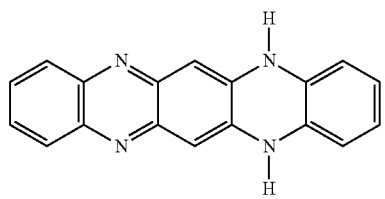
(3)

with a sulfonating agent to provide a compound of Formula 2:

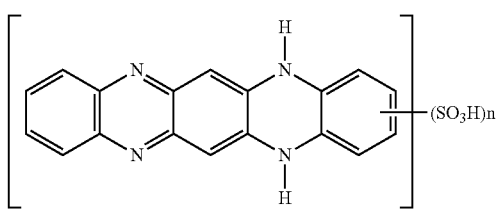
(2)

where n = 3 to 5 b. reaction of a compound of Formula 2 with a base to provide a compound of Formula 1.

The sulfonating agent may be selected from the group consisting of sulfuric acid, chlorosulfonic acid, and mixtures thereof.

Reaction of the compound of Formula 3 with a sulfonating agent may be conducted without solvent (i.e. neat), whereby the sulfonating agent acts as a reactant as well as solvent.

Reaction of the compound of Formula 3 with a sulfonating agent may be performed at elevated temperatures, ranging from about 80° C. to about 150° C., more preferably from about 100° to about 130° C., even more preferably from about 110° C. to about 130° C., and most preferably from about 120° to about 130° C.

The products of the reaction of a compound of Formula 3 with a sulfonating agent may be crystallized by the addition of a suitable co-solvent to the crude reaction product. The suitable co-solvent may be selected from the group consisting of water, aliphatic alcohols (e.g. methanol, butanol, ethanol, and isopropanol), ketones (e.g. acetone) and mixtures thereof.

The base may be selected from the group consisting of sodium hydroxide, sodium carbonate, sodium methoxide, and sodium acetate. In a preferred embodiment, following reaction with base, the pH of the reaction mixture may be adjusted to about 7 with an acid such as sulfuric acid prior to isolation of the compounds of Formula 1. Unexpectedly, we have found better conversion and yields than prior art processes when this pH adjustment is performed.

In illustrative embodiments of the present invention, there is provided a compound of Formula 2a:

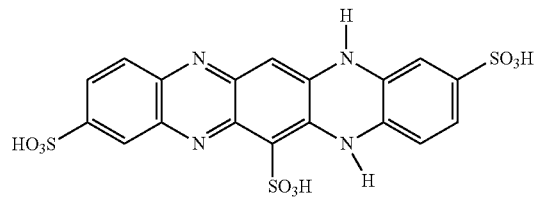
(2a)

In illustrative embodiments of the present invention, there is provided a compound of Formula 2a':

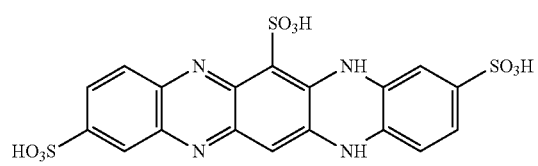
(2a')

In illustrative embodiments of the present invention, there is provided a compound of Formula 2b:

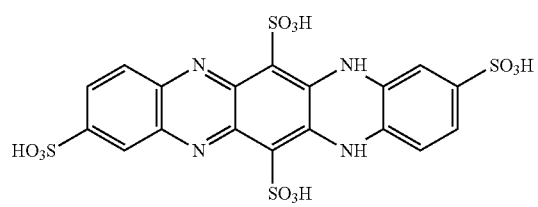
(2b)

In illustrative embodiments of the present invention, there is provided a compound of Formula 2c:

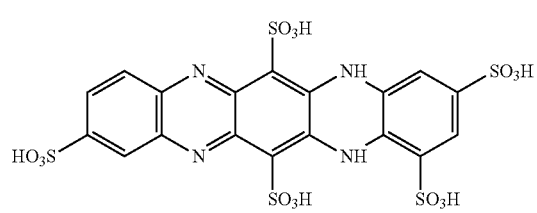
(2c)

In illustrative embodiments of the present invention, there is provided a compound of Formula 1a:

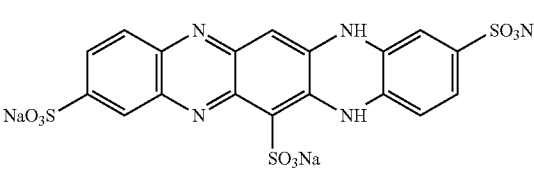
(1a)

In illustrative embodiments of the present invention, there is provided a compound of Formula 1a':

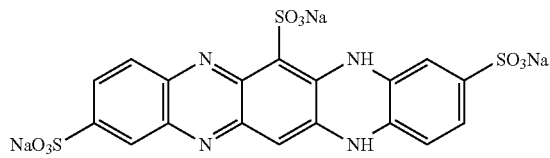

(1a′)

In illustrative embodiments of the present invention, there is provided a compound of Formula 1b:

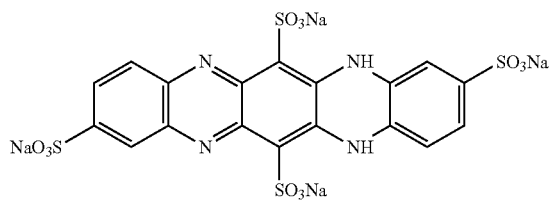

(1b)

In illustrative embodiments of the present invention, there is provided a compound of Formula 1c:

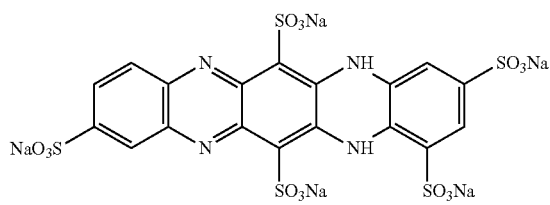

(1c)

EXAMPLES

The following examples are illustrative of some of the embodiments of the invention described herein. These examples should not be considered to limit the spirit or scope of the invention in any way.

Example 1

Preparation of 5,14-Dihydro-5,7,12,14-tetraazapentacene (3) (one pot process)

2,5-Dihydroxy-1,4-dibenzoquinone (4, 30.0 g, 0.2 mol) was added to a solution of o-phenylendiamine (5, 115.79 g, 1.1 mol) in benzyl alcohol (11.6 vol). The reaction mixture was heated to 135-140° C. and stirred for 20 hours. The reaction mixture was cooled to room temperature, and ethanol (120 mL) was added. The resulting suspension was filtered through a Buchner funnel and the solid was washed with ethanol (120 mL) and dried under vacuum in an oven at 60-70° C. to furnish 5,14-Dihydro-5,7,12,14-tetraazapentacene 3. Yield: 92%; HPLC purity: 99.56%.

$UV_{\lambda max}$ 285.0 nm.

Melting point: >350° C. (dec).

IR spectrum [KBr] (FIG. 1): 3100.4, 2922.5, 2352.1, and 1621.0 cm$^{-1}$.

$^1$H NMR (Trifluoroacetic acid-d): δ 7.4 (m, 4H), 7.32 (m, 4H), 7.05 (s, 2H) ppm

Example 2

Preparation and purification of sodium 5,14-dihydro-5,7,12,14-tetraazapentacene-2,6,9 (and 2,9,13)-trisulfonate (1a)

5,14-Dihydro-5,7,12,14-tetraazapentacene (3, 50 g, 0.18 mol) was added to chlorosulfonic acid (324 g, 2.78 mol) at 0-5° C. with stirring, and the reaction mixture temperature was allowed to rise to room temperature (3 h) and stirred for 8 h at room temperature. The reaction mixture was heated to 120° C. and stirred for 8 h. The reaction mixture was cooled to room temperature and added to water at 0° C. The resulting suspension obtained was stirred whereupon the solids were filtered, and washed with water (20 vol). The solid was added to water (16 vol) and the resulting suspension was stirred for 15 h at room temperature, cooled to 0-5° C., and charged with aqueous sodium hydroxide (145.6 g, 3.62 mol) to pH 12.5. The reaction mixture temperature was raised to room temperature and the reaction mixture was stirred for 12 h at which point the pH was adjusted to 7.0 with sulphuric acid and the suspension was stirred for 1 h, charged with alumina (150 g, 1.47 mol), and stirred for another 3 h at 20-25° C., filtered and the obtained filtrate distilled at reduced pressure until 15 vol. Then, the solution was charged with acetone (30 vol), and the resulting suspension was stirred for 2 h, filtered and washed with a mixture of acetone:water (2:1) (2 vol). The obtained filtrate was distilled at reduced pressure until 5 vol, and then charged with methanol (15 vol) and n-butanol (25 vol) and stirred for 1.5 (h) at 20-25° C. The reaction mixture was filtered, washed with methanol (2 vol) and dried under vacuum at 125° C. to provide sodium 5,14-dihydro-5,7,12,14-tetraazapentacene-2,6,9 (and 2,9,13)-trisulfonate.

The obtained compound was purified by column chromatography (alumina/water) (1a, 17.95 g, HPLC purity: 95%).

UV Spectrum (Acetonitrile/pH=2.5, 0.16 mg/mL):

| Wavelength (nm) | Absorbance (AU) |
| --- | --- |
| 291.1 | 1.300 |
| 366.0 | 0.130 |
| 569.6 | 0.550 |
| 613.6 | 0.630 |

| MS: SQ ESI (−) | | |
| --- | --- | --- |
| Ion observed | Observed (m/z) | Calculated (m/z) |
| $C_{18}H_9N_4S_3O_9H$ (2−) | 260.35 | 260.9805 |
| $C_{18}H_9N_4S_3O_9H$ + Na (1−) | 544.25 | 544.9507 |

Example 3

Preparation and purification of Sodium 5,14-dihydro-5,7,12,14-tetraazapentacene-2,6,9,13-tetrasulfonate (1b)

5,14-Dihydro-5,7,12,14-tetraazapentacene (3, 50 g, 0.18 mol) was added to a solution of chlorosulfonic acid (324 g, 2.78 mol) and processed as in example 2 to give Sodium 5,14-dihydro-5,7,12,14-tetraazapentacene-2,6,9,13-tetrasulfonate. This compound was purified by column chromatography (alumina/water) (1b, 12.3 g, HPLC: 99.74%, R.T. 12.129 min).

UV Spectrum (Acetonitrile/pH=2.5, 0.16 mg/mL):

| Wavelength (nm) | Absorbance (AU) |
|---|---|
| 218.4 | 0.105 |
| 286.9 | 0.620 |
| 502.0 | 0.260 |
| 536.0 | 0.250 |

| MS: SQ ESI (−) | | |
|---|---|---|
| Ion observed | Observed (m/z) | Calculated (m/z) |
| $C_{18}H_8N_4S_4O_{12}H_3$ (1−) | 602.92 | 602.9262 |
| $C_{18}H_8N_4S_4O_{12}H$ + Na (2−) | 311.95 | 311.9504 |
| $C_{18}H_8N_4S_4O_{12}H_2$ (2−) | 300.95 | 300.9594 |
| $C_{18}H_8N_4S_4O_{12}H$ (3−) | 200.30 | 200.3039 |

$^1$H NMR (CDCl3, 500 MHz) δ: 7.05 (s, 1H), 7.11 (d, 1H, J=8.30 Hz), 6.70 (d, 1H, J=8.35 Hz), 8.19 (s, 1H), 7.73 (d, 1H, J=8.85 Hz), 7.84 (d, 1H, J=8.80, Hz) ppm.
$^{13}$C NMR (CDCl3, 125 MHz) δ: 112.3, 137.5, 121.3, 115.2, 129.5, 139.0, 125.7, 141.4, 124.5, 129.3, 140.9, 126.8 ppm.

Example 4

Preparation and purification of sodium 5,14-dihydro-5,7,12,14-tetraazapentacene-2,4,6,9,13-pentasulfonate (1c)

5,14-Dihydro-5,7,12,14-tetraazapentacene (3, 50 g, 0.2 mol) was added to a solution of chlorosulfonic (324 g, 2.78 mol) acid and processed as in example 2 to give 5,14-dihydro-5,7,12,14-tetraazapentacene-2,4,6,9,13-pentasulfonate. This compound was purified by column chromatography (alumina/water). Weight: 5.7 g, yield 8.57%. HPLC purity 86.68% (R.T. 23.554 min)
UV Spectrum (Acetonitrile/pH=2.5, 0.16 mg/mL):

| Wavelength (nm) | Absorbance (AU) |
|---|---|
| 212.2 | 0.085 |
| 290.5 | 0.400 |
| 500.7 | 0.195 |
| 536.0 | 0.195 |

| MS: SQ ESI (−) | | |
|---|---|---|
| Ion observed | Observed (m/z) | Calculated (m/z) |
| $C_{18}H_7N_4S_5O_{15}H_3$ (2−) | 340.93 | 340.9373 |
| $C_{18}H_7N_4S_5O_{15}H_2$ + Na (2−) | 351.92 | 351.9282 |
| $C_{18}H_7N_4S_5O_{15}H$ + 2Na (2−) | 362.91 | 362.9192 |
| $C_{18}H_7N_4S_5O_{15}H_3$ + Na (1−) | 704.86 | 704.8643 |
| $C_{18}H_7N_4S_5O_{15}H_2$ + 2Na (2−) | 726.84 | 726.8463 |

$^1$H NMR (CDCl3, 500 MHz) δ: 7.12 (d, 1H, J=1.6 Hz), 7.47 (d, 1H, J=1.7 Hz), 8.23 (d, 1H, J=1.7 Hz), 7.91 (dd, 1H, J=1.8, 8.7 Hz), 7.91 (dd, 11H, J=8.4, Hz) ppm.
$^{13}$C NMR (CDCl3, 125 MHz) δ: 114.6, 136.5, 119.2, 127.6, 128.5, 139.2, 125.9, 141.9, 124.8, 129.4, 141.1, 126.8 ppm.

Example 5

Preparation of Sodium 5,14-dihydro-5,7,12,14-tetraazapentacene polysulfonates (1)

5,14-Dihydro-5,7,12,14-tetraazapentacene (3, 50 g, 0.2 mol) obtained following the method essentially described in example 1 was added to chlorosulfonic (324 g, 2.8 mol) acid and processed as in example 2 to give sodium 5,14-dihydro-5,7,12,14-tetraazapentacene-2,6,9 (and 2,9,13)-trisulfonate, 5,14-dihydro-5,7,12,14-tetraazapentacene-2,6,9,13-tetrasulfonate, 5,14-dihydro-5,7,12,14-tetraazapentacene-2,4,6,9,13-pentasulfonate salts in a ratio of 40:20:10 by HPLC area. Weight: 36.7 g, yield 51.11%.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. The invention includes all embodiments and variations substantially as hereinbefore described.

What is claimed is:
1. A one-pot process for the preparation of 5,14-dihydro-5,7,12,14-tetraazapentacene of Formula (3):

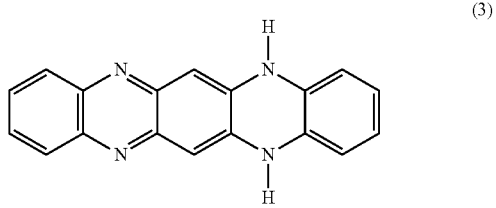 [SMILES: c1ccc2c(c1)Nc1cc3nc4ccccc4nc3cc1N2]

(3)

the process comprising reaction, in an alcohol solvent, of a compound of Formula (4):

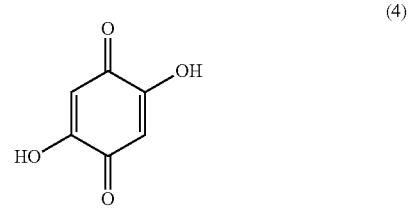

(4)

with a compound of Formula (5):

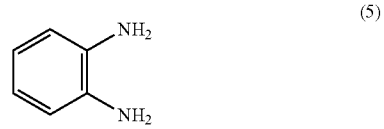

(5)

to provide a compound of Formula (3).
2. The process of claim 1 wherein the alcohol solvent is selected from the group consisting of benzyl alcohol, n-butanol, n-pentanol, cyclohexanol, glycol, and mixtures thereof.

3. The process of claim 2 wherein the alcohol solvent is benzyl alcohol.

4. The process of claim 2 wherein the glycol is diethylene glycol or polyethylene glycol.

5. The process of claim 1 wherein the compound of Formula (3) is isolated by the addition of a co-solvent selected from the group consisting of aliphatic alcohols and mixtures thereof.

6. The process of claim 5 wherein the co-solvent is ethanol.

* * * * *